United States Patent [19]

Duranleau et al.

[11] Patent Number: 4,691,041
[45] Date of Patent: Sep. 1, 1987

[54] PROCESS FOR PRODUCTION OF ETHYLENE GLYCOL AND DIMETHYL CARBONATE

[75] Inventors: Roger G. Duranleau, Georgetown; Edward C. Y. Nieh; John F. Knifton, both of Austin, all of Tex.

[73] Assignee: Texaco Inc., White Plains, N.Y.

[21] Appl. No.: 815,954

[22] Filed: Jan. 3, 1986

[51] Int. Cl.[4] .................... C07C 68/00; C07C 29/128; C07C 31/20
[52] U.S. Cl. ..................................... 558/277; 568/858
[58] Field of Search ......................... 568/858; 558/277

[56] References Cited

U.S. PATENT DOCUMENTS 3,880,939 4/1975 Corn et al. ........................... 568/858
4,062,884 12/1977 Romano et al. ..................... 558/277
4,519,875 5/1985 Becker et al. ................... 568/858 X

FOREIGN PATENT DOCUMENTS 57-14542 1/1982 Japan .................................. 568/858
58-150435 9/1983 Japan .................................. 568/858

Primary Examiner—J. E. Evans
Attorney, Agent, or Firm—Jack H. Park; Kenneth R. Priem; Cynthia L. Kendrick

[57] ABSTRACT

A process is disclosed for the preparation of ethylene glycol and dimethyl carbonate by reacting methanol and ethylene carbonate in the presence of a series of heterogenous catalyst systems including ion exchange resins with tertiary amine, quaternary ammonium, sulfonic acid and carboxylic acid functional groups, alkali and alkaline earth silicates impregnated into silica and ammonium exchanged zeolites.

11 Claims, 1 Drawing Figure

DIAGRAM OF PROCESS FOR SIMULTANEOUSLY MAKING ETHYLENE GLYCOL AND DIMETHYL CARBONATE

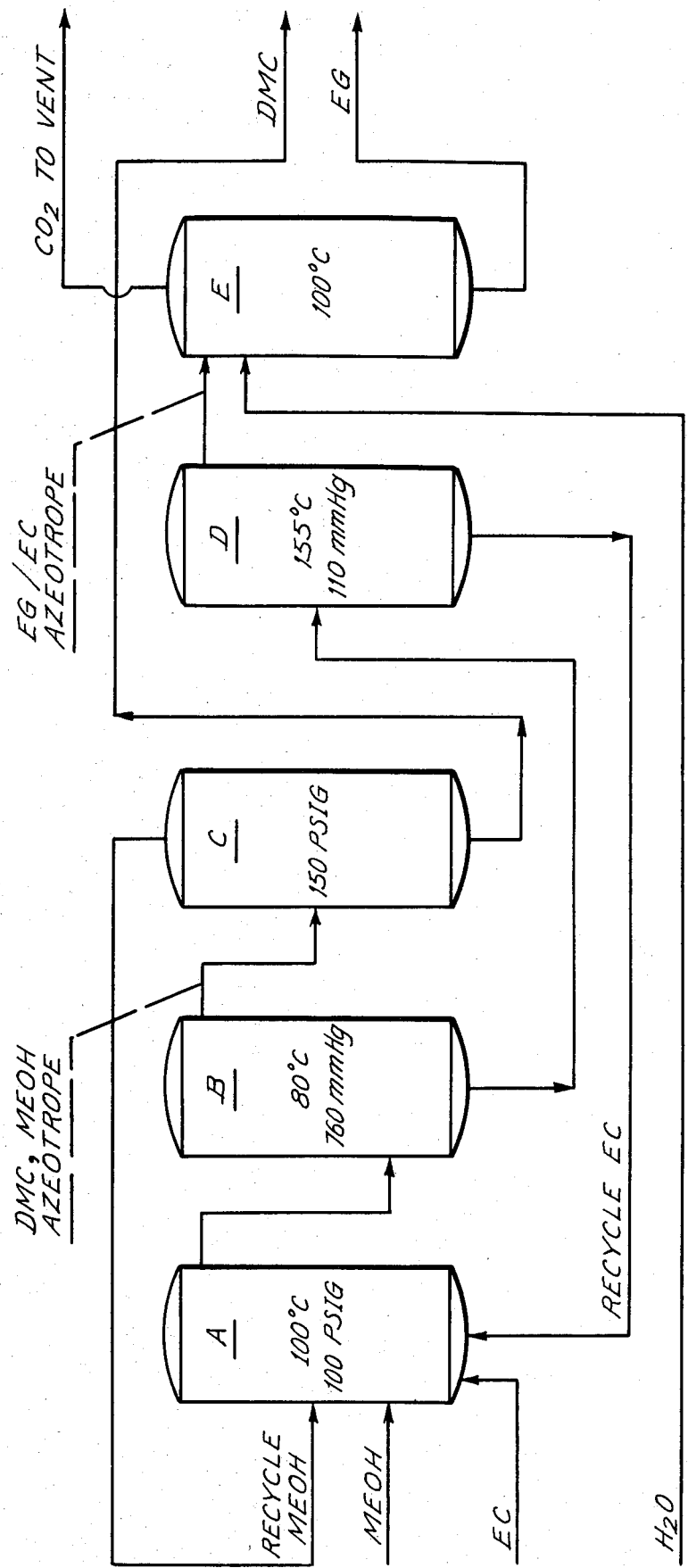

PROCESS FOR PRODUCTION OF ETHYLENE GLYCOL AND DIMETHYL CARBONATE

This invention concerns an improved process for preparing ethylene glycol and dimethyl carbonate by the transesterification reaction of ethylene carbonate and methanol in the presence of several classes of heterogenous catalysts, including macroreticular and gel type ion exchange resins with tertiary amine functional groups, ion exchange resins with quaternary ammonium functional groups, ion exchange resins with sulfonic acid groups, ion exchange resins with carboxylic acid functional groups, alkali and alkaline earth silicates on silica, and ammonium exchanged zeolites. The invention is particularly advantageous in that substantially fewer moles of methanol are needed in the methanol-ethylene carbonate feedstock per mole of dimethyl carbonate produced.

BACKGROUND OF THE INVENTION

Generally the prior art reports that the transesterification of aliphatic hydroxy compounds with carbonic acid, aliphatic diesters and aromatic diesters occurs readily in the presence of a basic catalyst and is a convenient method of synthesis of higher carbonates.

Several references deal with the transesterification of glycol carbonates using an aliphatic alcohol. Most demonstrate the use of methanol and ethylene carbonate.

There is taught in U.S. Pat. No. 3,803,201 a process for making dimethyl carbonate by methanolysis of alkylene carbonate wherein the improvement comprises removing the dimethyl carbonate from the reaction mixture during the reaction by distilling a mixture of methanol and dimethyl carbonate from the reaction mixture.

U.S. Pat. No. 4,307,032 discloses a process for the preparation of a dialkylcarbonate by contacting a glycol carbonate of a 1,2-diol with 2 to 4 carbon atoms with a selected alcohol to form the corresponding carbonate of said alcohol at a temperature of between 50 and 250° C., in the presence of an improved catalyst which is a thallium compound, so that the reaction can take place under milder conditions. Thallium is however expensive and very toxic.

In another process disclosed in U.S. Pat. No. 4,181,676 there is taught a method for preparation of dialkyl carbonate by contacting a glycol carbonate of a 1,2-diol having 2 to 4 carbon atoms with a selected group of alcohols at an elevated temperature in the presence of an alkali metal or alkali metal compound wherein the improvement comprises employing less than 0.01 percent by weight of alkali metal or alkali metal compound based on the weight of the reaction mixture.

It is known that alkyl carbonates of the type ROCOOR can be obtained from alcohols and cyclic carbonates corresponding to the above formula through a transesterification reaction in the presence of alkali alcoholates or hydrates; however, moderate amounts of inorganic compounds are produced by these reactions which must be removed by methods which may unfavorably affect the general economy of the process.

In U.S. Pat. No. 4,062,884 this problem was addressed and it was found that dialkylcarbonates can be prepared by reacting alcohols with cyclic carbonates in the presence of organic bases, which makes it unnecessary to remove inorganic compounds and allows the catalyst to be totally recovered by means of simple distillation. The preferred organic base is a tertiary aliphatic amine.

U.S. Pat. No. 4,349,486 teaches a monocarbonate transesterification process comprising contacting a beta-fluoroaliphatic carbonate, a compound selected from the class of monohydroxy aliphatic alcohols, monohydroxy phenols and ortho-positioned dihydroxy aromatic compounds in the presence of a base. This invention claims to greatly reduce undesirable side reactions and only small amounts of carbonic acid-aliphatic-aromatic mixed diester is associated with the isolated aromatic monocarbonate reaction.

The Gilpin and Emmons Patent, referred to above, discusses problems associated with the separation of the methanol, dimethyl carbonate azeotrope and teaches one solution, wherein dimethyl carbonate is isolated from the azeotrope by a combination of low temperature crystallization and fractional distillation.

In the art there are also discussions of the transesterification reaction and the general acid-base catalysis of such systems. For example, in *J. Am. Chem. Soc.* 96(a) 2924-9 (1974), Hine and Kluppel discuss enthalpies for the reactions of esters, such as trimethyl orthoformate, triethyl orthoformate, tetramethyl orthocarbonate etc. with excess 65% tetrahydrofuran-35% water in the presence of acid at 25° to give the corresponding simple esters and methanol or ethanol. Enthalpies of formation are calculated. It is found that the marked stabilization that accompanies the attachment of several alkoxy groups to the same saturated carbon atom may be illustrated by the disproportionation of dimethyl ether to tetramethyl orthocarbonate and methane.

In another article in the *J. Org. Chem.* 49(b) 1122-1125 (1984) Cella and Bacon discuss the results of their work. Among other things, they found that the alkylation of alkali metal bicarbonate and carbonate salts with alkyl halides in dipolar aprotic solvents and phase-transfer catalysts produces alkyl carbonates in good yields. The major limitation of this method is the failure of activated aryl halides or electronegatively substituted alkyl halides to produce carbonates due to the facility with which the intermediate alkoxy carbonate salts decompose.

Disadvantages of the methods discussed above include in many cases the fact that it is necessary to use a large amount of methanol feedstock relative to the amount of dimethyl carbonate produced. Also, in many cases alkali metal halides are coproduced and these present disposal problems.

It would be a substantial advance in the art to devise an efficient process for co-producing dimethyl carbonate and ethylene glycol which required only ca. 2-5 moles of methanol per mole of dimethyl carbonate produced. The dimethyl carbonate produced by this novel process could be used as a gasoline extender.

SUMMARY OF THE INVENTION

This invention concerns a process for the simultaneous production of ethylene glycol and dimethyl carbonate from ethylene carbonate and methanol which comprises reacting ethylene carbonate and methanol in the presence of several classes of heterogeneous catalyst including macrorecticular and gel type ion exchange resins with tertiary amine functional groups, ion exchange resins with quaternary ammonium functional groups, ion exchange resins with sulfonic acid groupings, ion exchange resins with carboxylic acid functional groups, alkali and alkaline earth silicates on silica, and ammonium exchanged zeolites, at a temperature of from 0° C. to 150° C. and an operative pressure of zero to 5000 psig, until the desired products are formed.

A particular advantage of these systems over the prior art is that lower molar concentrations of methanol are required in the methanol-ethylene carbonate feed in order to produce an equilibrium concentration of ethylene carbonate.

Other advantages to using the heterogeneous catalysts of this invention include.

(1) The high rates of the transesterification reaction achieved with these catalysts.
(2) The ease with which the catalyst can be removed from the reaction products.
(3) The lack of color bodies produced in the ester products.
(4) The economic advantages of recycling the recovered solid catalyst for reuse in further transesterification.
(5) The lack of corrosion of metal equipment.

DRAWINGS

FIG. 1 is a schematic illustration of the preferred process of the invention using a block diagram layout.

DETAILED DESCRIPTION OF THE INVENTION

In the narrower and more preferred practice of this invention dimethylcarbonate and ethylene glycol are prepared simultaneously by a transesterification process which comprises reacting ethylene carbonate and methanol in the presence of an ion exchange resin with tertiary amine functional groups, at a temperature of at least 50° C. and a pressure of at least 50 psig until the desired products are formed.

Starting materials employed in the process are an alcohol and an alkylene carbonate. Alcohols which work in the process of this invention include the monohydric alcohols containing one to 10 carbon atoms, including methanol, ethanol, isopropanol and isobutanol. Methanol is the preferred alcohol. Alkalene carbonates which will work in the process of this invention include the carbonate derivatives of 1,2-diols containing two to 10 carbon atoms per molecule, including ethylene carbonate, 1,2-propylene carbonate and 1,2-butanediol carbonate. Ethylene carbonate is the preferred alkylene carbonate feedstock for this process. The preferred starting materials are represented in FIG. 1. Recovery of the desired ethylene glycol and dimethyl carbonate can generally be carried out by distillation and crystallization.

More specifically, methanol and ethylene carbonate are fed into the transesterification reactor "A" in FIG. 1 in streams adjusted to maintain a mole ratio of methanol to ethylene carbonate of between 1:2 and 1:5. The reactor is maintained at a temperature of from 0° C. to 150° C. and a pressure of 0-5000 psig, and the methanol and ethylene carbonate are passed over a heterogeneous catalyst, producing as effluents methanol, dimethyl carbonate, ethylene glycol and ethylene carbonate. These effluents are channeled to a distillation tower, designated "B", where the methanol and dimethyl carbonate are removed as "overhead". This "overhead" fraction is sent to a second distillation tower, designated "C", wherein the overhead is distilled at about 10 atm to recover pure dimethyl carbonate as a "bottoms" product and methanol as an "overhead" product. The methanol is recycled to the first reactor "A", and the dimethyl carbonate is sent to storage. The bottoms from Tower "B" are sent to a fourth tower, designed as "D", and distilled at about 100 mm Hg wherein an overhead comprising an azeotrope of ethylene carbonate and ethylene glycol is produced and passed over a second catalyst bed, which catalyzes the addition of stoichiometric amounts of water to the ethylene carbonate in the azeotrope. This bed, designated as reactor "E" produces substantial quantities of ethylene glycol. The bottoms from "D", largely ethylene carbonate, are recycled to reactor "A".

This process is further described INFRA.

FIG. 1 shows that in Tower "C", the methanol, dimethyl carbonate azeotrope, produced in the ester exchange reactor "A", is separated, and the dimethyl carbonate is isolated in essentially pure form.

The heterogeneous catalyst systems suitable for the practice of this invention generally comprise an insoluble acid or base. At least six classes of heterogeneous catalysts have been found effective for the desired simultaneous production of ethylene glycol and dimethyl carbonate. They include:

(1) Macroreticular and gel type ion exchange resins with weakly basic functional groups, such as the tertiary amine functional group. In such resins the terminal amine function is bonded to an organic polymer backbone directly, or through one or more carbon atoms, or through a combination of carbon and nitrogen bonds. The tertiary amine function, may, for example, be the N,N-dimethylamine group or the N,N-diethylamine group. Such groups may be bonded directly, or indirectly to a polystyrene polymer backbone, that may be cross-linked with divinylbenzene. Alternately, the tertiary amine group may be bonded directly, or indirectly to an acrylic acid or methacrylic acid polymer that may also be cross-linked with divinylbenzene, or to a phenolic polymer.

Examples of such resins include the commercially available Amberlyst ® A-21 and Amberlite ® IRA-68 resins, marketed by Rohm and Haas, as well as the Amberlite ® IR-45 and XE-236 resins, and Duolite ® S-761.

(2) A second class of suitable heterogeneous catalysts is the ion exchange resins with strongly basic functional groups, such as the quaternary ammonium and phosphonium functional group. In such resins the quaternary ammonium function is bonded to an organic polymer backbone, either directly, or through one or more carbon atoms. The quaternary ammonium function may, for example, be the trimethylammonium hydroxide base, or the trimethylammonium chloride or trimethylammonium bromide groups bonded to a polystyrene backbone, that may be cross-linked with divinylbenzene. Examples of suitable resins of this class include the commercially available Amberlyst ® A-26 and A-27, Dowex ® 1 ×2-100 and Amberlite ® IRA-904, IRA-410 and IRA-400 (OH) resins, as well as Amberlite ® IRA-458.

(3) A third class of suitable catalysts is the ion exchange resins with strongly acidic cation exchange. These include the gel type or macroreticular ion exchange resins with sulfonic acid functional groups, wherein the sulfonic acid function is bonded directly or indirectly to an organic polymer backbone. Examples of such resins include the Amberlyst ® 15 and XN-1010, Amberlite ® IR-118, Dowex 50 x 2-100 and 5 x 8-100, XL-383 and -386, plus Bio Rad ® AG50W-X2 and Ambersep ® 252H.

(4) Also effective are weakly acidic ion exchange resins that may, for example, contain the carboxylic acid function. Here the polymer backbone of the resin may contain acrylic acid, methacrylic acid and styrene polymer units, and the carboxylic acid groups may be present as the free acid, or as the corresponding alkali or alkaline earth metal salt. Suitable examples include Amberlite ® IRP-64, IRC-84 and IRC-72.

(5) A fifth type of suitable catalysts is a class of heterogeneous catalysts comprising alkali and alkaline earth silicates impregnated into silica. Suitable examples include the lithium, sodium, potassium and calcium silicates impregnated into silica beads. A typical preparation of such a catalyst is illustrated in Example A.

(6) The sixth class of catalysts for the practice of this invention is certain ammonium exchanged zeolites. Particularly effective are ammonium exchanged Y-zeolites, such as the ammonium form of LZY-62, LZY-72 and LZY-82 marketed by Union Carbide.

The preferred class of catalyst for the cosynthesis of dimethyl carbonate and ethylene glycol is the macroreticular ion exchange resins with weakly basic functional groups such as the tertiary amine functional group.

During the cosynthesis of ethylene glycol and dimethyl carbonate by the reaction of ethylene carbonate with methanol, a large excess of methanol is normally employed in the prior art. Usually the initial molar ratio of methanol to ethylene carbonate is in the range of 5 or greater, and preferably at least 10. This preferred ratio range is illustrated by U.S. Pat. No. 3,803,201 (1974). In the practice of this invention, by contrast, the initial molar ratio of methanol to ethylene carbonate is preferably 2 to 5. Such a range of molar ratios is illustrated by the accompanying examples.

Potential advantages to operating at this lower methanol-to-ethylene carbonate molar ratio include the lower levels of methanol required to be recycled after the transesterification step in a process scheme such as described in FIG. 1.

Ethylene glycol-dimethyl carbonate synthesis using the classes of heterogeneous catalysts described SUPRA can be conducted at reaction temperatures in the range from 0° to 150° C. The preferred operating temperature range is 60°–120° C.

The reaction can be conducted under atmospheric pressure. A pressure reactor is nevertheless required in the case of low-boiling point components if the reaction is to be carried out in the upper temperature range and in the liquid phase. The pressure is not critical. In general the reaction is allowed to proceed under the autogenous pressure of the reactants. However, the reaction can also be carried out under elevated pressure, for example, under an inert atmosphere. A pressure of zero to 5000 psig is appropriate here. An operating pressure of greater than 50 psig is preferred.

The residence time for the ethylene carbonate and methanol reactants in the transesterification reactor ("A" in FIG. 1) may vary over a wide range according to the temperature of reaction, the molar ratios of carbonate/alcohol feedstocks, etc. Using the heterogeneous catalysts of this invention, the necessary residence time in the reactor may range from 0.1 hours to 10 hours, although it may be extended beyond 10 hours without danger of additional by-products being formed.

The preferred residence time is in the range of 0.5 to 4 hours.

The desired products of this process according to the invention are ethylene glycol and dimethyl carbonate. By-products include diethylene glycol and dimethyl ether.

Products have been identified in this work by gas chromatography (gc), NMR, IR and GCIR or a combination of these techniques. Analyses have, for the most part, been by g.c.; all temperatures are in degrees centigrade and all pressures in pounds per square inch gauge.

The following examples illustrate the novel process of this invention. The examples are only for illustrating the invention and are not considered to be limiting:

EXAMPLE I

This example illustrates the cosynthesis of ethylene glycol and dimethyl carbonate using, as the heterogeneous catalyst, a weakly basic ion exchange resin containing tertiary amine functional groups.

The synthesis was conducted in a tubular reactor (0.625" Dia.; 29" long), constructed of 316 stainless steel, operated upflow and mounted in a furnace, controllable to $\mp 1.0°$ C. and fitted with pumps allowing flow control of $< \mp 1$ ml/hr. The reactor was also fitted with a pressure regulating device and equipment for monitoring temperature, pressure and flow rate.

The reactor was charged at the beginning of the experiment with 100 cc of a weakly basic, macroreticular, ion exchange resin with N,N-dimethylamine functional groups bonded to a polystyrene polymer (Rohm and Haas Amberlyst ® A-21). A screen and glass beads were placed at the top and bottom of the reactor to ensure the resin would remain in the middle portion.

The catalyst bed was first conditioned by washing with methanol (100 cc/hr., 100° C.) for 40 hours. A solution of methanol (1185 g, 37.0 mole) plus ethylene carbonate (815 g, 9.3 mole) was then pumped through the catalyst bed at 100 cc/hr., while the reactor was held at 80° C., at a total pressure of 100 psig. Samples of the product liquid were taken periodically and material after three hours running time typically showed the following composition:

Dimethyl carbonate = 4.76%
Ethylene glycol = 1.86%
Methanol = 60.7%
Ethylene carbonate = 24.72%

EXAMPLES II-X

A series of ethylene glycol-dimethyl carbonate syntheses were conducted using the reactor, procedures and weakly basic ion exchange resin of Example I. In these examples the operating temperature was raised to 100° C.; the liquid hourly space velocity (LHSV) and total operating pressure (psig) were varied independently. The results are shown in Table I. It may be noted that:

(1) In Examples II and III, operating at a space velocity of 0.7–1:15, at 100° C. and 100 psig, produces close to an equilibrium mixture of dimethyl carbonate and ethylene glycol. In these examples the concentration of dimethyl carbonate in the crude product liquid exceeds 19%, while the concentration of ethylene glycol coproduct reaches 11%.

(2) In Examples VIII-X (in comparison with Example II etc.), total pressure appears to have little effect upon the product composition.

TABLE I

Effect of Conditions on Carbonate Exchange Reaction[a,b,c]

| Example | l HSV | Temp. °C. | Press. psig | %[d,e] MeOH | %[d,e] EG | %[d,e] EC | %[d,e] DMC |
|---|---|---|---|---|---|---|---|
| II | 1.15 | 100 | 100 | 54.0 | 11.0 | 13.2 | 19.1 |
| III | 0.7 | 100 | 100 | 53.4 | 11.4 | 13.6 | 19.6 |
| IV | 1.7 | 100 | 100 | 57.1 | 8.0 | 17.9 | 15.1 |
| V | 2.0 | 100 | 100 | 58.7 | 6.8 | 18.6 | 14.1 |
| VI | 4.25 | 100 | 100 | 57.8 | 6.2 | 21.8 | 8.4 |
| VII | 2.2 | 100 | 60 | 61.6 | 7.8 | 13.0 | 15.0 |
| VIII | 1.0 | 100 | 500 | 54.0 | 11.3 | 13.2 | 19.2 |
| IX | 1.0 | 100 | 1000 | 53.6 | 11.2 | 13.4 | 19.3 |
| X | 1.0 | 100 | 2000 | 53.7 | 11.2 | 13.4 | 19.2 |

[a]Feed = 4.0 mole methanol per mole of ethylene carbonate
[b]Catalyst = Rohm and Haas A21 resin conditioned for 40.0 hours prior to experiment.
[c]All work done in an upflow mode; see Example I for detailed description of reactor and procedure.
[d]Results determined by G.C., given in area percent
[e]MeOH = methanol; EG = ethylene glycol; EC = ethylene carbonate; DMC = dimethyl carbonate

EXAMPLES XI

This example illustrates the cosynthesis of ethylene glycol and dimethyl carbonate where the heterogeneous catalyst is another weakly basic ion exchange resin containing the tertiary amine functional group.

Using the reactor and procedures of Example I, the catalyst bed is comprised of 100 cc of a weakly basic, gel type, ion exchange resin with N,N-dimethylamine functional groups bonded indirectly to an acrylic acid polymer (Rohm and Haas Amerlite ® IRA-68) After conditioning the catalyst bed by washing with methanol (100 cc/hr., 100° C.) for 40 hr., a solution of methanol (1185 g, 37.00 mole) plus ethylene carbonate (815 g, 9.3 mole) was pumped through the bed at 100 cc/hr., while the reactor was held at 50° C. (for 4 hr.), 80° C. (for 20 hr.) and 100° C. (for 5 hr.). The total pressure in the reactor was maintained at 100 psig throughout this experiment. Samples of the product liquid were taken periodically at all three reaction temperatures, typical product compositions were as follows:

At 50° C.:
  Dimethyl carbonate=0.2%
  Ethylene glycol=0.1%
  Methanol=59.4%
  Ethylene carbonate=39.4%
At 80° C.:
  Dimethyl carbonate=16.5%
  Ethylene glycol=11.2%
  Methanol=47.2%
  Ethylene carbonate=23.9%
At 100° C.:
  Dimethyl carbonate=21.8%
  Ethylene glycol=15.5%
  Methanol=43.3%
  Ethylene carbonate=18.7%

It may be noted that in this example, operating the transesterification reaction at 100° C., with the IRA-68 ion exchange resin, the concentration of dimethyl carbonate in the crude product liquid is 21.8%, while the concentration of ethylene glycol coproduct is 15.5%.

EXAMPLE XII

This example illustrates the cosynthesis of ethylene glycol and dimethyl carbonate using another weakly basic ion exchange resin containing the tertiary amine functional group and a phenolic matrix structure.

Following the procedures of Example I, the catalyst bed, comprising 100 cc of Duolite ® S-761, is pretreated with methanol at 100° C. and then fed a standard solution of methanol (37.0 mole) plus ethylene carbonate (9.3 mole) at a pump rate of 100 cc/hr., while the reactor is held at 80° C. and 100 psig. Samples of the liquid product were taken periodically, material after 3 hours running time typically showed the following composition:

Dimethyl carbonate=6.0%
  Ethylene glycol=5.6%
  Methanol=71.4%
  Ethylene carbonate=5.6%

EXAMPLES XIII–XLIX

In this series, representative examples of five additional classes of heterogeneous catalysts were evaluated for the production of dimethyl carbonate and ethylene glycol. The reactor and procedures were as described in Example I. The results are shown in Tables II through V.

It may be noted that dimethyl carbonate—ethylene glycol cosynthesis from ethylene carbonate and methanol has been demonstrated with the following classes of catalysts.

(1) Ion exchange resins with strongly basic functional groups, such as the quaternary ammonium functional group. This is illustrated in Table II by Examples XIII through XXV for the Amberlyst ® A-26 and A-27, Dowex ® 1 x 2-100 and Amberlite ® IRA-904, IRA-410 and IRA-400(OH) resins over the temperature range 60-120° C.

(2) Ion exchange resins with strongly acidic cation exchange. This is illustrated in Table III for resins with the sulphonic acid functional groups by Examples XXVI through XXXVIII for Amberlyst ® 15 and XN-1010, Amberlite ® IR-118, Dowex ® 50 x 2-100 and 5×8-100, XL-383 and -386, plus Bio Rad ® AG 50W-X2 and Ambersep ® 252H at temperatures to 140° C.

(3) Weakly acidic ion exchange resins containing, for example, the carboxylic acid function. This is illustrated in Table IV by Examples XXXIX through XLIII for Amberlite ® IRC-72, IRC-84 and IRP-64.

(4) Alkali and alkaline earth silicates impregnated into silica. This class of catalyst is illustrated by Example XLIV and through XLVI in Table V.

(5) Ammonium exchanged zeolites. This class of catalyst is illustrated in Table V by Examples XLVII through XLIX.

TALE II[a]

EFFECT OF CATALYST STRUCTURE UPON THE METHANOL-ETHYLENE CARBONATE EXCHANGE REACTION - STRONGLY BASIC RESIN CATALYSTS

| Example | Catalyst | Supplier | Temp. (°C.) | LHSV | Product Composition (%)[b] | | | |
|---|---|---|---|---|---|---|---|---|
| | | | | | MeOH | EG | EC | DMC |
| XIII | Amberlyst ® A-26 | Rohm & Haas | 60 | 1.1 | 53.2 | 5.9 | 32.2 | 8.4 |
| XIV | Amberlyst ® A-26 | Rohm & Haas | 90 | 1.1 | 47.6 | 11.4 | 24.7 | 16.0 |
| XV | Amberlyst ® A-26 | Rohm & Haas | 110 | 1.1 | 44.1 | 15.1 | 19.4 | 21.1 |

TABLE II[a]-continued

EFFECT OF CATALYST STRUCTURE UPON THE METHANOL-ETHYLENE CARBONATE EXCHANGE REACTION - STRONGLY BASIC RESIN CATALYSTS

| Example | Catalyst | Supplier | Temp. (°C.) | LHSV | \multicolumn{4}{c}{Product Composition (%)[b]} |||| 
|---|---|---|---|---|---|---|---|---|
| | | | | | MeOH | EG | EC | DMC |
| XVI | Amberlyst ® A-27 | Rohm & Haas | 100 | 1.0 | 52.9 | 3.4 | 30.7 | 4.3 |
| XVII | Dowex ® 1 × 2-100 | Dow | 60 | 1.0 | 55.2 | 2.2 | 31.4 | 3.1 |
| XVIII | Dowex ® 1 × 2-100 | Dow | 80 | 1.0 | 51.9 | 4.1 | 36.6 | 5.4 |
| XIX | Dowex ® 1 × 2-100 | Dow | 100 | 1.0 | 48.5 | 9.1 | 27.8 | 12.8 |
| XX | Amberlite ® IRA-904 | Rohm & Haas | 100 | 1.0 | 57.1 | 0.5 | 40.7 | 0.7 |
| XXI | Amberlite ® IRA-904 | Rohm & Haas | 120 | 1.0 | 51.9 | 5.2 | 34.4 | 7.1 |
| XXII | Amberlite ® IRA-400(OH) | Rohm & Haas | 60 | 1.0 | 52.1 | 5.5 | 33.0 | 7.7 |
| XXIII | Amberlite ® IRA-400(OH) | Rohm & Haas | 80 | 1.0 | 44.4 | 13.3 | 22.8 | 18.5 |
| XXIV | Amberlite ® IRA-400(OH) | Rohm & Haas | 100 | 1.0 | 41.7 | 16.7 | 23.7 | 23.7 |
| XXV | Amberlite ® IRA-410 | Rohm & Haas | 100 | 1.0 | 46.9 | 10.6 | 26.3 | 14.6 |

[a]Operating conditions as per Example I.
[b]MeOH, methanol EG, ethylene glycol; EC, ethylene carbonate, DMC, dimethyl carbonate, results determined by G. C., given in weight percent.

TABLE III[a]

EFFECT OF CATALYST STRUCTURE UPON THE METHANOL-ETHYLENE CARBONATE EXCHANGE REACTION - STRONGLY ACIDIC RESIN CATALYSTS

| Example | Catalyst | Supplier | Temp. (°C.) | LHSV | MeOH | EG | EC | DMC |
|---|---|---|---|---|---|---|---|---|
| XXVI | Amberlyst ® 15 | Rohm & Haas | 120 | 1.0 | 45.5 | 3.6 | 15.2 | 7.9 |
| XXVII | Amberlyst ® XN-1010 | Rohm & Haas | 100 | 1.0 | 53.4 | 7.0 | 23.7 | 8.9 |
| XXVIII | Amberlyst ® IR-118 | Rohm & Haas | 100 | 1.0 | 47.9 | 11.3 | 24.8 | 13.8 |
| XXIX | Dowex ® 50 × 2-100 | Dow | 100 | 1.0 | 48.6 | 10.8 | 26.3 | 13.5 |
| XXX | Dowex ® 5 × 8-100 | Dow | 100 | 1.0 | 47.0 | 12.9 | 23.9 | 15.0 |
| XXXI | Dowex ® 5 × 8-100 | Dow | 120 | 1.0 | 43.1 | 21.7 | 15.3 | 16.4 |
| XXXII | Dowex ® 5 × 8-100 | Dow | 140 | 1.0 | 44.4 | 32.6 | 3.4 | 4.4 |
| XXXIII | XL-383 | Rohm & Haas | 90 | 1.0 | 58.1 | 8.7 | 27.4 | 4.5 |
| XXXIV | XL-386 | Rohm & Haas | 90 | 1.0 | 58.3 | 7.6 | 28.1 | 3.9 |
| XXXV | Bio Rad ® AG-50W-X2 | Bio Rad | 100 | 1.0 | 49.7 | 10.1 | 24.8 | 13.9 |
| XXXVI | Ambersep ® 252H | Rohm & Haas | 100 | 1.0 | 49.3 | 9.9 | 28.6 | 11.0 |
| XXXVII | Ambersep ® 252H | Rohm & Haas | 120 | 1.3 | 46.0 | 17.3 | 20.4 | 13.6 |
| XXXVIII | Ambersep ® 252H | Rohm & Haas | 140 | 1.0 | 44.6 | 31.2 | 3.1 | 5.5 |

[a]Operating conditions as per Example I.
[b]Designation as per Table II.

TABLE IV[a]

EFFECT OF CATALYST STRUCTURE UPON THE METHANOL-ETHYLENE CARBONATE EXCHANGE REACTION - WEAKLY ACIDIC RESINS

| Example | Catalyst | Supplier | Temp. (°C.) | LHSV | MeOH | EG | EC | DMC |
|---|---|---|---|---|---|---|---|---|
| XXXIX | Amberlite ® IRP-64 | Rohm & Haas | 100 | 1.0 | 58.3 | 0.1 | 40.6 | 0.1 |
| XL | Amberlite ® IRC-84 | Rohm & Haas | 100 | 1.0 | 60.9 | 0.1 | 38.6 | |
| XLI | Amberlite ® IRC-84 | Rohm & Haas | 140 | 1.0 | 56.0 | 0.3 | 42.9 | 0.2 |
| XLII | Amberlite ® IRC-72 | Rohm & Haas | 100 | 1.0 | 51.9 | 8.6 | 26.7 | 12.3 |
| XLIII | Amberlite ® IRC-72 | Rohm & Haas | 120 | 1.0 | 46.3 | 13.4 | 21.0 | 18.7 |

[a]Operating conditions as per Example I.
[b]Designation as per Table II.

TABLE V[a]

EFFECT OF CATALYST STRUCTURE UPON THE METHANOL-ETHYLENE CARBONATE EXCHANGE REACTION- TREATED SILICA AND ZEOLITE CATALYSTS

| Example | Catalyst | Temp. (°C.) | LHSV | MeOH | EG | EC | DMC |
|---|---|---|---|---|---|---|---|
| XLIV | NaSiO$_3$ on Silica[c] | 80 | 1.0 | 43.5 | 12.3 | 28.2 | 14.7 |
| XLV | KHSi$_2$O$_5$ on Silica[d] | 125 | 1.0 | 54.5 | 3.3 | 36.9 | 4.5 |
| XLVI | LiSiO$_3$ on Silica[d] | 125 | 1.0 | 55.1 | 1.7 | 31.9 | 2.7 |
| XLVII | Zeolite LZY-62, NH$_4$+ Form | 100 | 1.0 | 44.4 | 3.7 | 47.9 | 2.1 |
| XLVIII | Zeolite LZY-72, NH$_4$+ Form | 100 | 1.0 | 47.4 | 2.9 | 46.3 | 2.0 |
| XLIX | Zeolite LZY-82, NH$_4$+ Form | 100 | 1.0 | 49.4 | 3.1 | 42.1 | 3.3 |

[a]Operating conditions as per Example I.
[b]Designation as per Table II.
[c]For synthesis procedure: See Example A.
[d]Prepare by procedure similar to Example A.

EXAMPLE A

This example illustrates the preparation of the sodium silicate on silica catalyst employed in Table V, Example XLIV, for dimethyl carbonate-ethylene glycol cosynthesis.

Silica pellets (180 g, 3.0 mole, 3/16" Dia., 3/16" high) were soaked with water glass (400 cc, 32% Conc. of sodium silicate) for 40 hours. The pellets were then filtered off, spread on a stainless steel tray where they had no contact with each other, and calcined at Ca. 550° C. for 24 hours. The resultant material was then sieved to a 20 mesh screen. The weight of the pellets was 123 g.

Analyses of the pellets by atomic absorption showed a sodium content of 4.8%.

EXAMPLE L

A process description based on experimental data and literature data is shown in FIG. 1. FIG. 1 describes the system using a block diagram layout. In this process, methanol and ethylene carbonate are fed into the transesterification reactor "A" at such a rate that the space velocity is 1.2. The various streams are adjusted such that the total reactor input is maintained at a mole ratio of 4/1 (methanol/ethylene carbonate=4/1). The reactor is maintained at 100° C. and 100 psig. The catalyst is an ion exchange resin (Rohm and Haas Amberlyst® A-21) used as the free base and kept in the reactor by use of appropriate porous plugs. The reactor effluent, consisting of methanol (54.0%), dimethyl carbonate (19.1%), ethylene glycol (11.0%) and ethylene carbonate (13.2%) is sent to distillation tower "B" where the methanol and dimethyl carbonate are removed. The overhead consisting of methanol (72%) and dimethyl carbonate (28%) is sent to distillation tower "C" where the components are distilled at 10 atm. to recover pure dimethyl carbonate, as a bottoms product while methanol is taken overhead and is 95% pure. This stream is recycled to reactor "A". The bottoms from tower "B" are sent to tower "D" where they are distilled at 110 mm Hg. The overhead consists of the azeotrope of ethylene carbonate and ethylene glycol. Vapor liquid equilibrium data indicates this material will be a about 5-6% ethylene carbonate. This material is passed over another resin bed "E" (Amberlyst® A-21, same as above) after combining with 2 equivalents of water per mole of ethylene carbonate. This reactor "E" is also operated at a space velocity of 1.2 and maintained at 100° C. The effluent is ethylene glycol (98.9%) having a small amount of water (1.1%) and is sent to purification. The residue bottoms from tower "D" is largely ethylene carbonate and is recycled to reactor "A", thereby completing the system.

What is claimed is:

1. A process for producing ethylene glycol and dimethyl carbonate by reacting ethylene carbonate and methanol in the presence of a heterogeneous catalyst selected from the group consisting of ion exchange resins with quaternary ammonium functional groups, ion exchange resins with sulfonic, acid functional groups, ion exchange resins with carboxylic acid functional groups, alkali and alkaline earth silicates impregnated into silica, and ammonium exchanged zeolites, at a temperature of 0° to 150° C. until the desired products are formed.

2. The process of claim 1 wherein the initial molar ratio of methanol to ethylene carbonate is in the range of two to 5.

3. The process of claim 1 wherein the operating pressure is between 0 and 5000 psig.

4. The process of claim 1 for simultaneously producing dimethyl carbonate and ethylene glycol further comprising:

feeding methanol and ethylene carbonate into a transesterification reactor in streams adjusted to maintain a mole ratio of methanol to ethylene carbonate of between 2:1 and 5:1, maintaining the reactor at a temperature of from 60° to 120° C. and a pressure of at least 50 psig, passing said methanol and ethylene carbonate over an ion exchange resin in said reactor, producing as effluents methanol, dimethyl carbonate, ethylene glycol and ethylene carbonate, wherein said effluents are channeled to a distillation tower, removing the methanol and dimethyl carbonate as an overhead fraction, sending said overhead to a second distillation tower, while sending the bottoms to a third distillation tower, distilling said overhead in the second distillation tower at 10 atm to recover pure dimethyl carbonate as a bottoms product, removing methanol as an overhead product, recycling said "overhead" methanol to said first reactor, distilling said bottoms from the first tower at ca 100 mm Hg in the third tower, to produce an overhead comprising an azeotrope of ethylene carbonate and ethylene glycol and a residue which is recycled to the first reactor, and passing said overhead over a second resin bed with sufficient water to produce ethylene glycol.

5. The process of claim 1 wherein the ion exchange resin is one with quaternary ammonium functional groups.

6. The process of claim 1 wherein the ion exchange resin is one with sulfonic acid functional groups.

7. The process of claim 1 wherein the ion exchange resin is one with carboxylic acid functional groups.

8. The process of claim 1 wherein the alkali and alkaline earth silicate impregnated into silica is selected from the group consisting of sodium silicate, potassium silicate and lithium silicate.

9. The process of claim 1 wherein the ammonium exchanged zeolite is an ammonium exchanged Y-zeolite.

10. The process of claim 1 wherein the ion exchange resin with quaternary ammonium functional groups has a polystyrene backbone cross-linked with divinylbenzene.

11. The process of claim 1 wherein the ion exchange resin with carboxylic acid functional groups is a polystyrene or acrylic acid polymer cross-linked with divinyl benzene.

* * * * *